United States Patent [19]

Bernard

[11] Patent Number: 5,149,358
[45] Date of Patent: Sep. 22, 1992

[54] HERBICIDAL COMBINATION BASED ON BROMOXYNIL ALKANOATES AND 2-[[(4,6-DIMETHOXYPYRIMIDIN-2-YL)AMINOCARBONYL]AMINO-SULFONYL]-N,N-DIMETHYL-3-PYRIDINE CARBOXAMIDE

[75] Inventor: Thierry Bernard, Dardilly, France
[73] Assignee: Rhone-Poulenc Agrochimie, Lyons, France
[21] Appl. No.: 646,646
[22] PCT Filed: Jun. 7, 1990
[86] PCT No.: PCT/FR90/00401
 § 371 Date: Feb. 7, 1991
 § 102(e) Date: Feb. 7, 1991
[87] PCT Pub. No.: WO90/15535
 PCT Pub. Date: Dec. 27, 1990

[30] Foreign Application Priority Data

Jun. 13, 1989 [FR] France .................. 89 08154

[51] Int. Cl.⁵ ............... A01N 43/40; A01N 43/54; A01N 47/30; A01N 37/34
[52] U.S. Cl. .......................... 71/92; 71/105; 71/120
[58] Field of Search ..................... 71/92, 105

[56] References Cited

U.S. PATENT DOCUMENTS 4,786,734  11/1988  Hanagan .................. 546/293

FOREIGN PATENT DOCUMENTS 0232067  8/1987  European Pat. Off. .
0237292  9/1987  European Pat. Off. .
0303383  2/1989  European Pat. Off. .

OTHER PUBLICATIONS

The Agrochemicals Handbook, 2nd ed. "Bromaxymil". Aug. 1987.

Primary Examiner—Richard L. Raymond
Assistant Examiner—S. Mark Clardy
Attorney, Agent, or Firm—Burns, Doane, Swecker & Mathis

[57] ABSTRACT

Herbicidal combination having a synergistic effect as a result of the combination (a) of bromoxynil or one of its derivatives corresponding to the formula

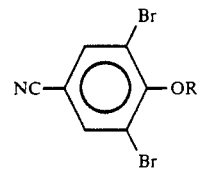

R=H, alkylcarbonyl or K, with (2-[[4,6-dimethoxypyrimidin-2-yl)aminocarbonyl]-aminosulphonyl]-N,N-dimethyl-3-pyridinecarboxamide (II))

Application to maize crops.

29 Claims, No Drawings

HERBICIDAL COMBINATION BASED ON BROMOXYNIL ALKANOATES AND 2-[[(4,6-DIMETHOXYPYRIMIDIN-2-YL)AMINOCARBONYL]AMINO-SULFONYL]-N,N-DIMETHYL-3-PYRIDINE CARBOXAMIDE

The present invention relates to a herbicidal product containing a synergistic combination of bromoxynil (I) or of one of its derivatives, and of 2-[[(4,6-dimethoxypyrimidin-2-yl) aminocarbonyl]amino-sulphonyl]-N,N-dimethyl-3-pyridinecarboxamide (II), which is remarkably suitable for the selective control of weeds in maize cultures. The invention likewise relates to the use of the novel product, optionally in the form of a composition by way of herbicide and to a method of controlling post-emergence weeds in maize cultures with the aid of the product or of the composition.

PRIOR ART

Bromoxynil or one of its derivatives is well known as a selective post-emergence broad-leaf herbicide in maize crops, in particular from the "Pesticide Manual", 8th edition. In contrast, this compound or one of its derivatives is little or not active against monocotyledon weeds.

Moreover, EP-A-232,067 and EP-A-237,292 disclose 2-[[(4,6-dimethoxypyrimidin-2-yl)aminocarbonyl]aminosulphonyl]-N,N-dimethyl-3-pyridinecarboxamide as herbicide, in particular selective post-emergence herbicide, in maize crops. These last two documents moreover mention that, in general, the N-pyrimidinyl-N-pyridinesulphonylureas can be combined with certain herbicides, inter alia bromoxynil. However, no combination of this type has been described.

European Patent Application No. 0,303,383 likewise mentions certain combinations with the herbicide described in EP-A-232,067, without giving any examples.

OBJECT OF THE INVENTION

Nevertheless, it is always desirable to improve the action of herbicidal active substances.

As far as the present invention is concerned, it proposes a novel combination which results from a limited choice from amongst a virtually infinite number of possibilities and which provides big advantages which will be better understood in the light of what will be described hereinafter.

In this way, it has been found in a completely unexpected manner, that the combination improved, in a noticeable and surprising fashion, the respective and isolated action of the two active substances for a certain number of weeds which are particularly harmful in crops, in particular maize, while preserving the selectivity towards the crops. From this follows an improvement of the activity spectrum and a possibility of reducing the respective dose of each active substance used, this latter quality being particularly important for ecological reasons which can be easily understood.

The combination therefore presents a remarkable degree of synergism as defined by PML Tammes, Netherlands Journal of Plant Pathology, 70 (1964) p. 7380 in an article with the title "Isoboles, une representation graphique de synergie dans les pesticides [Isoboles, a graphic representation of synergism in pesticides]", or as defined by Limpel, L. E., P. H. Schuldt and D. Lamont, 1962, Proc. NEWCC 16:48-53, using the formula:

$$E = X + Y - \frac{XY}{100}$$

where E is the expected percentage of growth inhibition of a mixture of the two herbicides at defined doses, X is the observed percentage of growth inhibition of herbicide A at a defined dose, Y is the observed percentage of growth inhibition of herbicide B at a defined dose. If the observed percentage of inhibition of the combination is greater than E, synergism is present.

In particular, the combination which is the object of the present invention has proven particularly effective for controlling:
Amaranthus retroflexus,
Echinochloa crus-galli,
Digitaria sanguinalis
Lolium multiflorum,
Polygonum convolvulus,
Solanum nigrum,
Ipomea hederacea.

THE PRODUCT ACCORDING TO THE INVENTION

The invention primarily relates to a product which contains a synergistic combination of bromoxynil or of one of these derivatives (I) and of 2-[[4,6-dimethoxypyrimidin-2-yl) aminocarbonyl]aminosulphonyl]-N,N-dimethyl-3-pyridinecarboxamide (II).

As far as bromoxynil or one of its derivatives is concerned, compounds which will be used in particular are those of formula:

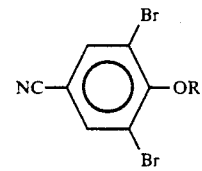

in which:

R is a hydrogen atom or a potassium or sodium atom or a CO-$C_2$-$C_{10}$ alkyl radical, preferably bromoxynil butanoate or heptanoate or octanoate.

The compound is preferably bromoxynil octanoate or heptanoate, or a mixture of the two.

In the case of the bromoxynil derivatives where R is a CO-$C_2$-$C_{10}$ alkyl radical, a combination will be used where the ratio of molar equivalents of (I) to the number of moles of (II) 2-[[4,6-dimethoxypyrimidin-2-yl) aminocarbonyl]aminosulphonyl]-N,N-dimethyl-3-pyridinecarboxamide is between 0.2 and 50, preferably 0.5 and 18.

In the case where the bromoxynil derivatives are in phenolic form (R=H), a combination will be used in which the molar ratio of (I) to II is between 1 and 100, preferably 1.5 and 60.

Most frequently, the combinations are of the binary type, but sometimes ternary or quaternary combinations with one or more other compatible pesticides can be envisaged.

THE USE ACCORDING TO THE INVENTION

Another object of the invention is the use of said products by way of herbicides, in particular in maize crops.

These products according to the invention are intended for simultaneous or separate use, or use staggered over a period of time, for the herbicidal treatment of undesirable plants, in particular against weeds which are present in maize crops.

In the case of simultaneous use (which is preferred), ready-to-use products can be used which contain the combination of the abovedescribed active substances. Likewise, products which have been prepared just before application can be used, by extemporaneously mixing active substances as they are described hereinafter.

Equally, the use can consist in using the product by treating the crops to be protected in succession with one and then the other of the active substances of formula (I) and (II), in such a way as to form the product according to the invention in situ on the plant.

The use of the products according to the invention is mostly effected in the form of a herbicidal composition which contains one or more agriculturally acceptable carriers and/or one or more surface-active agents.

In this way, in the case of extemporaneous preparations, each active substance can be in the form of a composition. In contrast, in the case of a ready-to-use mixture, it is the combination itself which is in the form of a composition.

These compositions which can be used as herbicidal agents contain, in addition to the active substance or the combination (whether it is an extemporaneous preparation or a ready-to-use mixture), solid or liquid agriculturally acceptable carriers and likewise agriculturally acceptable surface-active agents. Those which can be used, in particular, are the customary inert carriers and the customary surface-active agents. These compositions are likewise part of the invention.

These compositions can also contain a variety of other ingredients such as, for example, protective colloids, adhesives, thickeners, thixotropic agents, penetrants, stabilisers, sequestering agents, etc. More generally, the active substances or combinations used in the invention can be combined with all solid or liquid additives which correspond to customary formulation techniques.

In a general manner, the compositions according to the invention usually contain from approximately 0.05 to 95 % (by weight) of the active substance or of a combination according to the invention.

The term "carrier" in the present account is understood to mean an organic or inorganic, natural or synthetic substance with which the product or the combination is combined to facilitate its application on the plant. This carrier is solid (clays, natural or synthetic silicates, silica, resins, waxes, solid fertilisers, etc.) or liquid (solvent).

The surface-active agent can be an emulsifier or dispersant, or a wetting agent of the ionic or non-ionic type, or a mixture of such surface-active agents. Examples which may be mentioned are salts of phenolsulphonic or naphthalenesulphonic acids, polycondensates of ethylene oxide with fatty alcohols or with fatty acids or with fatty amines, substituted phenols (in particular alkylphenols or arylphenols), salts of esters of sulphosuccinic acids, taurine derivatives (in particular alkyltaurates), phosphoric esters of ethylene oxide/alcohol or ethylene oxide/phenol polycondensates, esters of fatty acid and of polyols, or derivatives of the preceding compounds which have sulphate, sulphonate and phosphate functions.

In the case of the ready-for-use preparations, the formulation which can be used is advantageously a suspoemulsion or a flowable, preferably in an organic phase such as described in EP-A-313,317, or a wettable powder, depending on the cases. If bromoxynil is in ester form, the formulation can be a suspoemulsion obtained, for example, by emulsifying an emulsifiable concentrate of bromoxynil, such as Buctril 20 (200 g/l), or Buctril 21 (225 g/l), which are mentioned in the Pesticide Manual, 8th edition, in a flowable in an organic or aqueous phase of 2-[[(4,6-dimethoxypyrimidin-2-yl)aminocarbonyl]aminosulphonyl]-N,N-dimethyl-3-pyridinecarboxamide, such as described in EP-A-237,292 page 46 Example No. 14.

The formulation can also be a flowable in organic phase, obtained by simply dissolving bromoxynil ester in the technical product state in a flowable in organic phase of 2-[[(4,6-dimethoxypyrimidin-2-yl) aminocarbonyl]aminosulphonyl]-N,N-dimethyl-3-pyridinecarboxamide such as described in EP-A-313,317. If bromoxynil is in the form of potassium salt or sodium salt, the formulation is a flowable obtained by mixing a bromoxynil solution in water with the same flowable as that described previously in the case of 2-[[(4,6-dimethoxypyrimidin-2-yl)aminocarbonyl]aminosulphonyl]-N,N-dimethyl-3-pyridinecarboxamide, or a wettable powder. If bromoxynil is in the form of a phenol, the formulation is a flowable obtained by mixing a bromoxynil flowable such as litarol (250 g/l), which is mentioned in the Pesticide Manual, and a flowable of 2-[[(4,6-dimethoxypyrimidin-2-yl) aminocarbonyl]aminosulphonyl]-N,N-dimethyl-3-pyridinecarboxamide, as described above, or alternatively, a wettable powder.

In the case of the products which are prepared just before use by extemporaneous mixture, it is possible to use the well-known preparation forms of bromoxynil or its derivatives and the preparation forms of 2-[[(4,6-dimethyl-3-pyridinecarboxamide which are given in Patent Applications EP-A-232,067, 237,292 and 313,317.

TREATMENT METHOD ACCORDING TO THE INVENTION

The invention likewise concerns a method for controlling weeds, in particular in a site where crops grow, or where crops are intended to be grown, in particular maize, which method consists in applying an effective dose of product (or a composition containing it), such as has just been described previously.

During the application, the dose should be sufficient for controlling the growth of the weeds without causing substantial permanent damage to said crops. By effective dose there is understood, precisely in this context, the dose which allows this result to be obtained.

Application is effected post-emergence. Post-emergence is understood to mean application to the aerial or exposed parts of the weeds which have emerged from the soil surface.

The application is preferably done from the 2-3 leaf stage of the crop onwards to the 5-6 leaf stage, which corresponds approximately to a treatment of 15 days after the crop has emerged up to five months.

The following may be mentioned from amongst the weeds which can be controlled by said product: *Chenopodium hybridum, Chenopodium polyspermum, Chenopodium album, Amaranthus retroflexus, Amaranthus hybridus, Polygonum pensylvanicum, Polygonum lapathifolium, Polygonum persicaria, Ambrosia artemisiifolia, Ambrosia trifida, Xanthium pensylvanicum, Xanthium strumarium, Bidens pilosa, Ipomea spp, Solanum nigrum, Mercurialis annua, Portulaca oleracca, Sinapis arvensis, Atriplex patula, Atriplex hastata, Datura stramonium, Brassica nigra, Cassia obtusifolia, Convolvulus arvensis, Abutilon theophrasti, Sesbania exaltata, Polygonum convolvulus, Reseda lutea, Raphanus raphanistrum, Hypericum perforatum, Helianthus annuus, Galinsoga ciliata, Conyza canadensis, Euphorbia helioscopia.* From amongst the weeds for which a particularly unexpected herbicidal effect is observed, there are mentioned: *Echinochloa crus galli* and *Digitaria sanguinalis.*

The quantities of product containing the active substances of formula (I) and (II) can vary according to the nature of the weeds, of the crop and when the product is applied to said crop, of the composition used, of the period of application, or of the climatic circumstances.

Taking into account these factors, between 100 and 500 g of product will generally be applied per hectare in the case of bromoxynil derivatives in ester form. But it must be well understood that lower or higher doses can be used according to the particular problem to be solved.

Preferably, between 200 and 400 g of product will be applied per hectare.

Another preferred object of the invention is: a method of controlling weeds selected from amongst *Echinochloa crus galli* or *Digitaria sanguinalis* in maize fields, post-emergence of said maize and said weeds, by foliar application on said weeds, in the form of a herbicidal composition according to the invention, of 30 to 50 g per hectare of II (2-[[4,6-dimethoxypyrimidin-2-yl) aminocarbonyl]aminosulphonyl]-N,N-dimethyl-3-pyridinecarboxamide) and 200 to 300 g of bromoxynil octanoate, preferably 225 to 275 g/ha of bromoxynil octanoate.

Taking into account these factors, between and 900 g/ha of product will generally be applied in the case of bromoxynil in phenol form, naturally with the reservation that lower or higher doses can be used according to the particular problem to be solved.

Preferably, between 500 and 800 g of product will be applied per hectare in this case.

The invention will now be described in relation to concrete embodiments which are, of course, given for information only and can in no way limit the range of said invention. In order to simplify the method and to achieve a better base for comparison, the following were selected:
*Echinochloa crus-galli,*
*Lolium multiflorum,*
*Polygonum convolvulus,*
*Solanum nigrum,*
*Ipomea hederacea.*
to demonstrate the activity of the product according to the invention in maize crops.

GENERAL EXPERIMENTAL SET-UP

Application is effected after the plant species have emerged.

A number of seeds chosen as a function of the plant species and of the size of the seeds is sown in $7 \times 7 \times 8$ cm pots filled with light agricultural soil.

The seeds are subsequently covered by a layer of soil of thickness about 3 mm, and the seed is allowed to germinate until it gives rise to a plantlet at the convenient stage. The treatment stage in the case of the Gramineae is the "formation of second leaf" stage. The treatment stage for the dicotyledons is the "unfolded cotyledons, first true leaf being developed" stage.

The pots are then treated by spraying spray liquor in a quantity which corresponds to an application rate, by volume, of 500 1/ha, and which contains the active substance to be sprayed.

The liquor used for the treatment is a solution of active substances in an acetone/water mixture in the ratio 50/50, containing Cemulsol NP 10 (surface-active agent) which consists of an ethylene oxide/alkylphenol polycondensation product, in particular of an ethylene oxide/nonylphenol polycondensation product, and of Tween 20 (surface-active agent composed of an oleate of a sorbitol/ethylene oxide polycondensation product) in a ratio of 50% by weight of active substances.

The pots are then placed in containers intended to receive irrigation water, by way of irrigation from beneath, and maintained for 24 days at ambient temperature and a relative humidity of 70 %.

After 24 days, the number of live plants in the pots treated with liquor containing the active substance to be tested is counted, and the number of live plants in a control pot treated under the same conditions but by means of a liquor which does not contain active substance. In this way, the destruction percentage of the treated plants is determined in relation to the untreated control. A destruction percentage of 100% indicates that the plant species under consideration has been destroyed completely, and a percentage of 0% indicates that the number of live plants in the treated pot is identical to that of the control pot.

EXAMPLE 1

Experiment showing the nature of the synergistic biological effect of the combination of bromoxynil octanoate (I) and 2-[[4,6-dimethoxypyrimidin-2-yl) aminocarbonyl]aminosulphonyl]-N,N-dimethyl-3-pyridinecarboxamide (II) on *Echinochloa crus-galli.*

The experiment is carried out having sown seeds of *Echinochloa crus-galli.*

The table hereinafter represents the average of two tests in the greenhouse.

|  |  | I g/ha | | | | |
|---|---|---|---|---|---|---|
|  |  | 0 | 16 | 31 | 62 | 125 |
| II g/ha | 0 | 0 | 0 | 0 | 0 | 0 |
|  | 8 | 50.5 | 61.5 | 61.5 | 80.5 | 75 |

With reference to the formula given at the beginning of the description, the results given in the table above clearly show the excellent, and even unexpected, degree of synergism obtained using the combination of the invention.

EXAMPLE 2

Test showing the nature of the synergistic biological effect of the combination bromoxynil octanoate (I) and 2-[[4,6-dimethoxypyrimidin-2-yl) aminocarbonyl]aminosulphonyl]-N,N-dimethyl-3-pyridinecarboxamide (II) on *Lolium multiforum*

The experiment is carried out having sown *Lolium multiflorum* seeds.

The table below represents the average of two tests:

|  |  | I g/ha |  |  |  |  |
|---|---|---|---|---|---|---|
|  |  | 0 | 16 | 31 | 62 | 125 |
| II g/ha | 0 | 0 | 0 | 0 | 6 | 9.5 |
|  | 8 | 34 | 72 | 68 | 61.5 | 60.5 |

Referring to the formula given at the beginning of the description, the results given in the table above show clearly the excellent and unexpected degree of synergism obtained with the combination of the invention.

EXAMPLE 3

Test showing the nature of the synergistic biological effect of the combination bromoxynil octanoate (I) and 2-[[4,6-dimethoxypyrimidin-2-yl) aminocarbonyl]aminosulphonyl]-N,N-dimethyl-3-pyridinecarboxamide](II) on *Polygonum convolvulus*

The experiment is carried out having sown *Polygonum convolvulus* seeds.

The table below represents the average of two tests:

|  |  | I g/ha |  |  |  |  |
|---|---|---|---|---|---|---|
|  |  | 0 | 16 | 31 | 62 | 125 |
| II g/ha | 0 | 0 | 0 | 10 | 29 | 81 |
|  | 16 | 46 | 50 | 69 | 88 | 100 |
|  | 31 | 59 | 68 | 77 | 98.5 | 99.5 |

Referring to the formula given at the beginning of the description, the results given in the table below show clearly the excellent and unexpected degree of synergism obtained with the combination of the invention.

EXAMPLE 4

Test showing the nature of the synergistic biological effect of the combination bromoxynil octanoate (I) and 2-[[4,6-dimethoxypyrimidin-2-yl) aminocarbonyl]aminosulphonyl]-N,N-dimethyl-3-pyridinecarboxamide](II) on *Solanum nigrum*

The experiment is carried out having sown *Solanum nigrum* seeds.

The table below represents the average of two tests:

|  |  | I g/ha |  |  |  |  |
|---|---|---|---|---|---|---|
|  |  | 0 | 16 | 31 | 62 | 125 |
| II g/h | 0 | 0 | 16 | 29.5 | 82 | 86.5 |
|  | 16 | 65.5 | 71 | 72.5 | 98.5 | 98.5 |

Referring to the formula given at the beginning of the description, the results given in the table above show clearly the excellent and unexpected degree of synergism obtained with the combination of the invention.

EXAMPLE 5

Test showing the nature of the synergistic biological effect of the combination bromoxynil octanoate (I) and 2-[[4,6-dimethoxypyrimidin-2-yl) aminocarbonyl]aminosulphonyl]-N,N-dimethyl-3-pyridinecarboxamide](II) on *Ipomea hederacea*

The experiment is carried out having sown *Ipomea hederacea* seeds.

|  |  | I g/ha |  |  |  |  |
|---|---|---|---|---|---|---|
|  |  | 0 | 16 | 31 | 62 | 125 |
| II g/ha | 0 | 0 | 0 | 0 | 42 | 83 |
|  | 16 | 62 | 62 | 80 | 90 | 93 |

Referring to the formula given at the beginning of the description, the results given in the table above show clearly the excellent and unexpected degree of synergism obtained with the combination of the invention.

EXAMPLE 6

Test showing the absence of phytotoxicity of the combination bromoxynil octanoate (I) - [2-[[4,6-dimethoxypyrimidin-2-yl) aminocarbonyl]amidosulphonyl]-N,N-dimethyl-3-pyridinecarboxamide](II) on *Zea mais*

The experiment, having been set up as above but after having sown maize seeds, leads to the results given in the table below:

|  |  | I g/ha |  |  |  |  |
|---|---|---|---|---|---|---|
|  |  | 0 | 16 | 31 | 62 | 125 |
| II g/ha | 0 | 0 | 0 | 0 | 0 | 0 |
|  | 8 | 0 | 0 | 0 | 0 | 0 |
|  | 16 | 0 | 0 | 0 | 0 | 0 |
|  | 31 | 0 | 0 | 0 | 0 | 0 |

It is therefore noticed that the combination bromoxynil octanoate - [2-[[4,6-dimethoxypyrimidin-2-yl)aminocarbonyl]aminosulphonyl]-N,N-dimethyl-3-pyridinecarboxamide]shows no phytotoxicity whatsoever on the crop while increasing the respective activity of the two substances on the weeds given by example.

EXAMPLE 7

Test showing the absence of phytotoxicity of the combination of the phenol form of bromoxynil (I)[2-[[4,6-dimethoxypyrimidin-2-yl)aminocarbonyl]aminosulphonyl]-N,N-dimethyl-3-pyridinecarboxamide] (II) on *Zea mais*

The experiment, having been set up as above but after having sown maize seeds, leads to the results given in the table below:

|  |  | I |  |  |  |  |
|---|---|---|---|---|---|---|
|  |  | 0 | 31 | 62 | 125 | 250 |
| II | 0 | 0 | 0 | 0 | 0 | 0 |
|  | 8 | 0 | 0 | 0 | 0 | 0 |
|  | 16 | 0 | 0 | 0 | 0 | 0 |
|  | 31 | 0 | 0 | 0 | 0 | 0 |

It is therefore noticed that the combination phenol form of bromoxynil - [2-[[4,6-dimethoxypyrimidin-2-yl) aminocarbonyl]aminosulphonyl]-N,N-dimethyl-3- pyridinecarboxamide]shows no phytotoxicity whatsoever on the crop while increasing the respective activity of the two active substances on the weeds given by example.

EXAMPLE 8

Test showing the synergistic biological effect of the combination phenol form of bromoxynil (I) -[2-[4,6-dimethoxycyrimidin-2-yl)aminocarbonyl-]aminosulphonyl]-N,N-dimethyl-3-pyridinecarboxamide] (II) on *Echinochloa crus galli*

|         |   | \multicolumn{5}{c}{II g/ha} |
|---------|---|---|---|---|---|---|
|         |   | 0 | 31 | 62 | 125 | 250 |
| II g/ha | 0 | 0 | 0 | 0 | 0 | 0 |
|         | 8 | 50.5 | 41.5 | 61.5 | 61.5 | 52 |

The table above represents the average of 2 tests.

EXAMPLE 9

Test showing the synergistic biological effect of the combination phenol form of bromoxynil (I) - [2-[4,6-dimethoxypyrimidin-2-yl)aminocarbonyl-]aminosulphonyl]-N,N-dimethyl-3-pyridinecarboxamide] (II) on *Lolium multiflorum*

|         |   | \multicolumn{5}{c}{I g/ha} |
|---------|---|---|---|---|---|---|
|         |   | 0 | 31 | 62 | 125 | 250 |
| II g/ha | 0 | 0 | 0 | 0 | 3 | 6 |
|         | 8 | 34 | 40 | 60 | 59.5 | 53 |

The table above represents the average of 2

EXAMPLE 10

Test showing the synergistic biological effect of the combination phenol form of bromoxynil (I) - [2-[4,6-dimethoxypyrimidin-2-yl)aminocarbonyl-]aminosulphonyl]-N,N-dimethyl-3-pyridinecarboxamide] (II) on *Polygonum convolvulus*

|         |   | \multicolumn{5}{c}{I g/ha} |
|---------|---|---|---|---|---|---|
|         |   | 0 | 31 | 62 | 125 | 250 |
| II g/ha | 0 | 0 | 0 | 27 | 58.5 | 98.5 |
|         | 8 | 46 | 53 | 60.5 | 99 | 99 |

The table above represents the average of 2 tests.

EXAMPLE 11

Test showing the synergistic biological effect of the combination phenol form of bromoxynil (I) -[2-[4,6-dimethoxypyrimidin-2-yl)aminocarbonyl-]aminosulphonyl]-N,N-dimethyl-3-pyridinecarboxamide] (II) on *Ipomea hederacea*

|         |   | \multicolumn{5}{c}{I g/ha} |
|---------|---|---|---|---|---|---|
|         |   | 0 | 31 | 62 | 125 | 250 |
| II g/ha | 0 | 0 | 0 | 3 | 6 | 56 |
|         | 8 | 62 | -56 | 72 | 68 | 88 |

The table above represents the average of 2 tests.

EXAMPLE 12

Test showing the synergistic biological effect of the combination phenol form of bromoxynil (I) -[2-[4,6-dimethoxypyrimidin-2-yl)aminocarbonyl]aminosulphonyl]-N,N-dimethyl-3-pyridinecarboxamide] (II) on *Amaranthus retroflexus*

The experiment is carried out having sown seeds of *Amaranthus retroflexus*. With reference to the formula given at the beginning of the description, the results given in the table below show clearly the excellent and unexpected degree of synergism obtained with the combination of the invention.

|         |   | \multicolumn{5}{c}{I g/ha} |
|---------|---|---|---|---|---|---|
|         |   | 0 | 31 | 62 | 125 | 250 |
| II g/ha | 0 | 0 | 6 | 10 | 15.5 | 36.5 |
|         | 8 | 59.5 | 66.5 | 69 | 69 | 98.5 |

Field experiment with maize crops

The field was divided into plots of equal size. The species were sown in each plot, in rows at a distance of 15 cm. These species embraced the following monocotyledons:

Cockspur grass: *Echinochloa crus-galli* (ECHCG)
Hairy fingergrass: *Digitaria sanguinalis* (DIGSA)

When these plants have reached the 3-6 leaf stage, that is to say about three weeks after sowing, liquors obtained in the following fashion are applied to them:

Before application, a flowable of sulphonylurea containing 40 g/l of active substance is mixed with water. An emulsifiable concentrate of bromoxynil octanoate containing 250 g/l of active substance (Buctril) is added to obtain the liquor. Said liquor is subsequently applied. An untreated plot is arranged in proximity with each treated plot for comparison and assessment. These assessments are carried out after a predetermined period given for each test and they are expressed in destruction percentages for each species in comparison with the same species in each untreated plot.

Test in field I (Spain)

The application volume of the liquor is 300 l/ha, the point in time of application is when the weeds are, on average, in the 3-6 leaf stage, and the point in time of assessment is 5 to 12 days after th treatment in the case of maize and 27 days in the case of weeds. The following results are obtained:

|          | Maize |    |       |       |
|----------|-------|----|-------|-------|
|          | 5     | 12 | ECHCG | DIGSA |
| 40       | 0     | 0  | 62    | 67    |
| 250 + 40 | 10    | 5  | 100   | 70    |
| 60       | 0     | 0  | 100   | 80    |

A very powerful synergism with bromoxynil octanoate is observed while this herbicide has absolutely no action on the Gramineae. Furthermore, the slight phytotoxicity which is observed on day 5 is rapidly eliminated, and the crop plant recovers completely very rapidly.

Test in field II (Spain)

The application volume is identical to the one above. The average point in time of application is in the 3-6 leaf stage in the case of the weeds and the 3-4 leaf stage in the case of maize. The point in time of assessment is 12 days in the case of maize and 26 days in the case of the weeds, after the treatment. The following results are obtained.

|       | Maize | ECHCG | DIGSA |
|-------|-------|-------|-------|
| 40    | 0     | 95    | 72    |
| 250 + 40 | 2  | 100   | 70    |
| 60    | 0     | 100   | 70    |

Likewise, a strong synergism is observed for the dose 40/250.

Test in field III (France)

The application volume is identical to the one above. The average point in time of application is in the 2-3 leaf stage in the case of maize and in the stage of 2 emerged leaves in the case of the weeds. The following results are obtained.

|       | Maize | DIGSA |
|-------|-------|-------|
| 40    | 0     | 25    |
| 250 + 40 | 5  | 40    |
| 60    | 5     | 15    |
| 250 + 60 | 5  | 35    |

Test in field IV (France)

The application volume is 380 l/ha. The average point in time of the application is in the 2-3 leaf stage in the case of the weed and in the 5-7 leaf stage in the case of maize.

The following results are obtained.

|       | ECHCG |
|-------|-------|
| 40    | 30    |
| 250 + 40 | 87 |
| 60    | 65    |
| 250 + 60 | 77 |

Test in field V (France)

The application volume is 500 l/ha. The point in time of application is in the 3-5 leaf stage in the case of the weed. The assessment is carried out 52 days after the treatment.

The following results are obtained.

|       | ECHCG |
|-------|-------|
| 40    | 50    |
| 250 + 40 | 82 |
| 60    | 72    |
| 250 + 60 | 90 |

In conclusion, these results show the perfectly unexpected synergistic action with the absence of the action of bromoxynil octanoate on the Gramineae.

I claim:

1. A herbicidal composition comprising a synergistic herbicidally effective amount of:
   (a) at least one compound of the formula

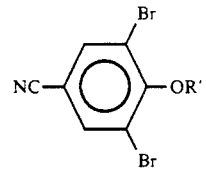

wherein R' is a $C_2$-$C_{10}$ alkylcarbonyl group; and
   (b) 2-[[(4,6-dimethoxypyrimidin-2-yl)aminocarbonyl-]aminosulphonyl]-N,N-dimethyl-3-pyridinecarboxamide).

2. The composition as claimed in claim 2, wherein the ratio in molar equivalents of (a) to (b) is between about 0.2 and about 50.

3. The composition as claimed in claim 2, wherein the ratio in molar equivalents of (a) to (b) is between about 0.5 and about 18.

4. The composition as claimed in claim 1, wherein (a) is selected from the group consisting of (1) bromoxynil heptanoate, (2) bromoxynil octanoate, and (3) a mixture of bromoxynil heptanoate and bromoxynil octanoate.

5. The composition as claimed in claim 1, further comprising an agriculturally acceptable carrier and/or an agriculturally acceptable surfactant.

6. The composition as claimed in claim 5, wherein the combined amount of (a) and (b) is from about 0.5 to about 95% by weight of the total composition.

7. A herbicidal composition comprising a synergistic herbicidally effective amount of:
   (a) bromoxynil octanoate; and
   (b) 2-[[(4,6-dimethoxypyrimidin-2-yl)aminocarbonyl-]aminosulphonyl]-N,N-dimethyl-3-pyridinecarboxamide.

8. The composition as claimed in claim 7, wherein the ratio in molar equivalents of (a) to (b) is between about 0.2 and about 50.

9. The composition as claimed in claim 8, wherein the ratio in molar equivalents of (a) to (b) is between about 0.5 and about 18.

10. The composition as claimed in claim 7, further comprising an agriculturally acceptable carrier and/or an agriculturally acceptable surfactant.

11. The composition as claimed in claim 10, wherein the combined about of (a) and (b) is from about 0.5 to about 95% by weight of the total composition.

12. A method for controlling weeds in a location in which maize is grown, said method comprising applying to said location, after said weeds have emerged, a synergistic herbicidally effective amount of:
   (a) at least one compound of the formula

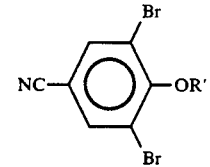

wherein R' is a $C_2$-$C_{10}$ alkylcarbonyl group and
   (b) 2-[[(4,6-dimethoxypyrimidin-2yl)aminocarbonyl-]aminosulphonyl]-N,N-dimethyl-3-pyridinecarboxamide.

13. The method as claimed in claim 12, wherein the ratio in molar equivalents of (a) to (b) is between about 0.2 and about 50.

14. The method as claimed in claim 13, wherein the ratio in molar equivalents of (a) to (b) is between about 0.5 and about 18.

15. The method as claimed in claim 12, wherein (a) is selected from the group consisting of (1) bromoxynil heptanoate, (2) bromoxynil octanoate, and (3) a mixture of bromoxynil heptanoate and bromoxynil octanoate.

16. The method as claimed in claim 12, wherein the amount of (a) and (b) applied is between about 100 and about 500 g/ha.

17. The method as claimed in claim 16, wherein the amount of (a) and (b) applied is between about 200 and about 400 g/ha.

18. The method as claimed in claim 12, wherein the weeds are selected from the group consisting of *Polygonum convolvulus, Lolium multiflorum, Solanum nigrum, Echinochloa crus-galli, Amaranthus retroflexus, Ipomea hederacea* and *Digitaria sanguinalis.*

19. The method as claimed in claim 12, wherein application is made when the maize is between the 2–3 leaf stage and the 5–6 leaf stage inclusive.

20. A method for controlling weeds in a location in which maize is grown, said method comprising applying to said location, after said weeds have emerged, a synergistic herbicidally effective amount of:
    (a) bromoxnil octanoate; and
    (b) 2-[[(4,6-dimethoxypyrimidin-2-yl)aminocarbonyl]aminoosulphonyl]-N,N-dimethyl-3-pyridinecarboxamide.

21. The method as claimed in claim 20, wherein the ratio in molar equivalents of (a) to (b) is between about 0.2 and about 50.

22. The method as claimed in claim 21, wherein the ratio in molar equivalents of (a) to (b) is between about 0.5 and about 18.

23. The method as claimed in claim 20, wherein the amount of (a) and (b) applied is between about 100 and about 500 g/ha.

24. The method as claimed in claim 23, wherein the amount of (a) and (b) applied is between about 200 and about 400 g/ha.

25. The method as claimed in claim 20, wherein the weeds are selected from the group consisting of *Polygonum convolvulus, Lolium multiflorum, Solanum nigrum, Echinochloa crus-galli, Amaranthus retroflexus, Ipomea hederacea* and *Digiteria sanguinalis.*

26. A method for controlling weeds selected from the group consisting of *Echinochloa crus-galli* and *Digitaria sanguinalis* in maize fields after the maize and the weeds have emerged, said method comprising applying to the leaves of said weeds from about 200 to about 300 grams per hectare of bromoxynil octanoate and from about 30 to about 50 grams of hectare of 2-[[(4,6-dimethoxypyrimidin-2-yl)aminocarbonyl]aminosulphonyl]-N,N-dimethyl-3-pyridinecarboxamide).

27. The method as claimed in claim 26, wherein application is made when the maize is between the 2–3 leaf stage and the 5–6 leaf stage inclusive.

28. The method as claimed in claim 26, wherein from about 225 to about 275 grams per hectare of bromoxynil octanoate are applied.

29. The method as claimed in claim 27, wherein from about 225 to about 275 grams per hectare of bromoxynil octanoate are applied.

* * * * *